United States Patent [19]

Klenk et al.

[11] 4,144,269
[45] Mar. 13, 1979

[54] PROCESS FOR THE PRODUCTION OF BENZOYL CYANIDE (IV)

[75] Inventors: Herbert Klenk, Hanau; Theodor Lüssling, Konstanz; Alfred Maierhofer, Allensbach; Heribert Offermanns, Hanau; Hans Wagner, Konstanz, all of Fed. Rep. of Germany

[73] Assignee: Deutsche Gold- und Silber-Scheideanstalt vormals Roessler, Frankfurt, Fed. Rep. of Germany

[21] Appl. No.: 802,943

[22] Filed: Jun. 2, 1977

[30] Foreign Application Priority Data

Apr. 18, 1977 [DE] Fed. Rep. of Germany ....... 2717075

[51] Int. Cl.$^2$ ..................... C07C 51/54; C07C 120/00
[52] U.S. Cl. ................................................. 260/545 R
[58] Field of Search ................................... 260/545 R

[56] References Cited

U.S. PATENT DOCUMENTS 4,069,252   1/1978   Findeisen et al. .................... 260/545

OTHER PUBLICATIONS

Koenig, "Tetrahedron Letters No. 26", pp. 2275–2278 (1974).
Migrdichian, "Organic Synthesis", pp. 420–423 (1957).
Thesing et al., Angewandte Chemie, vol. 68, pp. 425–448 (1956).

*Primary Examiner*—Gerald A. Schwartz
*Attorney, Agent, or Firm*—Cushman, Darby & Cushman

[57] ABSTRACT

Benzoyl cyanide is made from benzoyl chloride and an alkali metal cyanide in a two phase system comprising water and an inert organic solvent which has only slight miscibility with water in the presence of a tertiary amine and hydrogen cyanide.

28 Claims, No Drawings

PROCESS FOR THE PRODUCTION OF BENZOYL CYANIDE (IV)

BACKGROUND OF THE INVENTION

The invention is directed to a process for the production of benzoyl cyanide by reaction of benzoyl chloride with an alkali metal cyanide in a two phase system containing water and an organic solvent. Benzoyl cyanide is an important intermediate product for the production of herbicides.

It is known to produce benzoyl cyanide by the action of more than stoichiometrical amounts of copper (I) cyanide on benzoyl chloride. The reaction is carried out at temperatures up to 80° C. in acetonitrile or benzonitrile or in ether with the addition of more than stoichiometrical amounts of lithium chloride or lithium iodide (Normant et al, Bull. Soc. Chim. France (1972) pages 2402–2403) or at temperatures of 220 to 230° C. in the absence of a solvent (Org. Synth. Coll. 3, 112-114). At best these processes give a yield of 65%.

It is also known to produce benzoyl cyanide from benzoyl chloride by reaction with water free hydrogen cyanide and an at least equimolar amount of pyridine (Z. Phys. Chem. 192 (1943), 200–201). This process gives yields of 78%.

It is furthermore known to convert benzoyl chloride to benzoyl cyanide by means of an alkali cyanide in a two phase system consisting of water and a solvent which is immiscible with water in the presence of a quaternary alkyl ammonium salt (Koeing, Tetrahedron Letters No. 26 (1974), pages 2275 to 2278). In this process the yield only amounts to 60%.

A disadvantage of these known processes is that there are formed byproducts to a considerable extent, particularly the dimer of benzoyl cyanide (the benzoyloxyphenyl malodinitrile). Consequently, not only is the yield unsatisfactory but also its purity. Benzoyl cyanide can be separated from its dimer only with considerable difficulty and even then only incompletely.

SUMMARY OF THE INVENTION

There has now been found a process production of benzoyl cyanide from benzoyl chloride and an alkali metal cyanide in a two phase system comprising water and an organic solvent characterized by carrying out the reaction in the presence of a tertiary amine and hydrogen cyanide. According to this process it is possible to recover a pure benzoyl cyanide in a yield of over 80%.

The reaction of the invention is carried out in a two phase system comprising water and an organic solvent which is inert to the reactants and is only slightly miscible in water. The reaction of the invention is carried out in an organic solvent which is inert to the reactants. As the solvent there can be used for example ethers, e.g., dialkyl ethers, such as diethyl ether, dibutyl ether and diamyl ether, aromatic hydrocarbons and haloaromatic hydrocarbons, such as ethyl benzene, mesitylene, cumene, p-cymene, t-butyl benzene or 1,3,5-triethyl benzene, especially benzene, toluene, xylene, chlorobenzene and dichlorobenzene. Especially suited are aliphatic hydrocarbons, such as ligroin with a boiling range of 90 to 140° C., octane, decane, pentane, hexane and heptane, and particularly halogenated aliphatic hydrocarbons, such as chloroform, dichloroethylene, symmetrical tetrachloroethane, carbon tetrachloride, trichloroethylene, trimethylene bromide dibromoethylene, ethylene dibromide and especially methylene chloride. There can also be used mixtures of these solvents. Cycloaliphatic hydrocarbons, such as cyclohexane, decalin and tetralin can also be used.

There can be used widely varying amounts of water and organic solvent as desired. In a given case the amount is adjusted according to the type of organic solvent. Generally it is advantageous that there be present at the beginning of the reaction per mole of benzoyl chloride 50 to 250 ml of water and 300 to 1000 ml of organic solvent, especially 65 to 180 ml of water and 500 to 800 ml of organic solvent.

According to the invention the benzoyl chloride is reacted with the alkali metal cyanide in the presence of hydrogen cyanide. As alkali metal cyanide there is chiefly employed potassium cyanide and especially sodium cyanide. There can also be used lithium cyanide. There can be used either stoichiometric amounts or less or larger amounts of the alkali metal cyanide required to react with the benzoyl chloride. Generally, it is suitable to add at least about 0.8 mole and at most about 2.0 moles of alkali metal cyanide per mole of benzoyl chloride. Advantageously there are used about 0.9 to 1.2 moles, especially 1.00 to 1.05 moles of alkali cyanide per mole of benzoyl chloride. The hydrogen cyanide can be used in equimolar or in less or larger amounts per mole of benzoyl chloride. Generally, it is suitable to employ at least about 0.1 and at most about 3.0 moles of hydrogen cyanide per mole of benzoyl chloride. Advantageously there are employed about 0.5 to 1.5 moles, especially 0.9 to 1.2 moles are hydrogen cyanide per mole of benzoyl chloride.

According to the invention the reaction is carried out in the presence of tertiary amines. As such, there can be used for example N,N-dialkyl aralkylamines, especially N,N-dialkylbenzyl amines or N,N-dialkyl-$\beta$-phenylethylamines, such as N,N-dimethylbenzyl amine, N,N-diethyl benzyl amine, N,N-dimethyl-$\beta$-phenylethylamine and N,N-diethyl-$\beta$-phenylethyl amine or N,N-diaralkyl alkylamine, especially N,N-dibenzyl alkamines or N,N-di-$\beta$-phenylethyl alkyl amines such as N,N-dibenzyl methyl amine, N,N-dibenzyl ethyl amine, N,N-di-$\beta$-phenylethyl methyl amine and N,N-di-$\beta$-phenylethyl ethyl amine. Especially suited is N,N-dimethyl benzylamine. The alkyl group in the N,N-dialkyl aralkylamine is usually 1 to 2 carbon atoms.

Generally it is suitable to use at least about 0.001 mole of amine, but not more than about 0.1 mole of amine per mole of benzoyl chloride. It is advantageous to add about 0.005 to 0.05 mole of amine especially 0.01 to 0.02 mole of amine per mole of benzoyl chloride.

The reaction of the invention suitably takes place at temperature below about 50° C. Preferably the temperature is between −10 to +40° C., especially between −5 and +30° C.

The reaction can be carried out discontinuously or continuously, for example in a reaction tube with intensive mixing. A particularly suitable procedure is to add the benzoyl chloride as a solution in the organic solvent and to add the alkali cyanide as a solution in water, preferably as a solution of about 10 to 50 weight percent, especially of about 30 weight percent. Preferably the solution of the benzoyl chloride in the organic solvent together with the tertiary amine is present in the reactor and next it is treated with the hydrogen cyanide followed by addition of the aqueous alkali cyanide solution. If necessary the mixture is cooled so that the temperature does not exceed 50° C. and preferably does not exceed 30° C.

Unless otherwise indicated, all parts and percentages are by weight.

The materials employed can comprise, consist essentially of or consist of those set forth.

DESCRIPTION OF THE PREFERRED EMBODIMENTS

EXAMPLE 1

140.5 grams (1.0 mole) of benzoyl chloride were dissolved in 600 ml of methylene chloride. This solution was treated simultaneously with 27 grams (1.0 mole) of hydrogen cyanide and 1.83 grams (0.014 mole) of N,N-dimethyl benzyl amine and then cooled to 0° C. Then there were dropped in within 30 minutes a solution of 51 grams (1.04 moles) of sodium cyanide in 65 grams of water which had a temperature of 50° C. The temperature of the reaction mixture meanwhile and for a further 2 hours was held at 0° C. Subsequently the mixture was freed from separated solids. The liquid phases were separated and the organic phase was worked up by distillation to benzoyl cyanide with recovery of the excess hydrogen cyanide and the solvent. There were accumulated 135 grams of crude 93 percent benzoyl cyanide. This was purified by fractional distillation. There were recovered 123 grams of pure benzoyl cyanide (boiling point at 11 mbar 86 to 88° C.). This corresponds to a yield of 94% based on the benzoyl chloride employed.

EXAMPLE 2

140.5 grams (1.0 mole) of benzoyl chloride were dissolved in 600 ml of methylene chloride. This solution was treated simultaneously with 27 grams (1.0 mole) of hydrogen cyanide and 1.83 grams (0.014 mole) of N,N-dimethyl benzyl amine. Then within 20 minutes there were fed in 171 grams of a 29.8 percent aqueous sodium cyanide solution (1.04 moles of sodium cyanide). The temperature of the reaction mixture meanwhile and for a further 2 hours was held at 15 to 35° C. Then there were added 60 grams of water and the phases separated. After removal of the hydrogen cyanide and the methylene chloride there were obtained by distillation 136 grams of crude, 91 percent benzoyl cyanide. In fractional distillation there were obtained 122 grams of pure benzoyl cyanide. This corresponds to a yield of 93% base on the benzoyl chloride employed.

EXAMPLE 3

The procedure was the same as in Example 2 except that instead of the sodium cyanide solution there was added a solution of 65 grams of potassium cyanide (1.0 mole) in 120 ml of water. The yield of pure benzoyl cyanide was 121 grams, corresponding to 92% based on the benzoyl chloride employed.

EXAMPLE 4

The procedure was the same as in Example 2 except that instead of 600 ml of methylene chloride there were used in each case 600 ml of different solvent as shown in the following table.

| Solvent | Yield of Pure Benzoyl Cyanide |
| --- | --- |
| (a) chloroform | 92% |
| (b) carbon tetrachloride | 83% |
| (c) 1,2-dichloroethane | 89% |
| (d) 1,1-dichloroethane | 92% |
| (e) trichloroethylene | 79% |
| (f) gasoline (B.P. 40 to 60° C) | 87% |

EXAMPLE 5

The procedure of Example 2 was followed, but the hydrogen cyanide was used in different amounts as shown by the following table.

| Mole of Hydrogen cyanide Per Mole of Benzoyl Chloride | Yield of Pure Benzoyl Cyanide |
| --- | --- |
| (a) 0.1 | 86% |
| (b) 0.2 | 88% |
| (c) 0.5 | 89% |
| (d) 1.5 | 89% |

EXAMPLE 6

The procedure of Example 2 was followed, but the temperature of the reaction mixture during the feeding in of the sodium cyanide solution and the next 2 hours was held at −8 to −5° C. The yield of pure benzoyl cyanide based on the benzoyl chloride added was 91%.

EXAMPLE 7

The procedure of Example 2 was employed, but instead of N,N-dimethyl benzyl amine there was employed 0.014 mole of N,N-dimethyl-β-phenylethyl amine. The yield of benzoyl cyanide based on the benzoyl chloride was 73%.

What is claimed is:

1. A process for the production of benzoyl cyanide comprising reacting benzoyl chloride and an alkali metal cyanide in a two phase system comprising water and an inert organic solvent which is only slightly miscible with water, said reaction being carried out in the presence of a tertiary amine and hydrogen cyanide, said tertiary amine being an N,N-dialkyl aralkyl amine or an N,N-diaralkyl alkyl amine.

2. A process according to claim 1 wherein there is used about 0.9 to 1.2 moles of alkali cyanide per mole of benzoyl chloride.

3. A process according to claim 2 wherein there is used about 0.5 to 1.5 moles of hydrogen cyanide per mole of benzoyl chloride.

4. A process according to claim 3 wherein there is used 0.005 to 0.05 mole of tertiary amine per mole of benzoyl chloride.

5. A process according to claim 4 wherein the tertiary amine is N,N-dimethyl benzyl amine.

6. A process according to claim 5 wherein the reaction is carried out at a temperature of −10 to +40° C.

7. A process according to claim 1 wherein the alkali cyanide is sodium cyanide or potassium cyanide.

8. A process according to claim 1 wherein there is used about 0.8 to 2.0 moles of alkali cyanide per mole of benzoyl chloride.

9. A process according to claim 8 wherein there is used 0.9 to 1.2 moles of alkali cyanide per mole of benzoyl chloride.

10. A process according to claim 9 wherein there is used 1.00 to 1.05 moles of alkali cyanide per mole of benzoyl chloride.

11. A process according to claim 1 wherein there is used about 0.1 to 3.0 moles of hydrogen cyanide per mole of benzoyl chloride.

12. A process according to claim 11 wherein there is used about 0.5 to 1.5 moles of hydrogen cyanide per mole of benzoyl chloride.

13. A process according to claim 12 wherein there is used about 0.9 to 1.2 moles of hydrogen cyanide per mole of benzoyl chloride.

14. A process according to claim 1 wherein there is used about 0.001 to 0.1 mole of tertiary amine per mole of benzoyl chloride.

15. A process according to claim 14 wherein there is used about 0.005 to 0.05 mole of tertiary amine per mole of benzoyl chloride.

16. A process according to claim 15 wherein there is used about 0.01 to 0.02 mole of tertiary amine per mole of benzoyl chloride.

17. A process according to claim 1 wherein the alkyl groups of the tertiary amine are lower alkyl groups.

18. A process according to claim 1 wherein the tertiary amine is an N,N-dialkyl benzyl amine, an N,N-dialkyl-$\beta$-phenylethyl amine, an N,N-dibenzyl alkyl amine or an N,N-di-$\beta$-phenylethyl alkyl amine.

19. A process according to claim 18 wherein the alkyl group contains 1 to 2 carbon atoms.

20. A process according to claim 19 wherein the tertiary amine is N,N-di lower alkyl benzyl amine.

21. A process according to claim 20 wherein the tertiary amine is N,N-dimethyl benzyl amine.

22. A process according to claim 1 wherein the reaction is carried out at a temperature below about 50° C.

23. A process according to claim 22 wherein the temperature is between $-10$ and $+40°$ C.

24. A process according to claim 1 wherein there is used 50 to 250 ml of water and 300 to 1000 ml of organic solvent per mole of benzoyl chloride.

25. A process according to claim 1 wherein the organic solvent is a dialkyl ether, an aromatic hydrocarbon, a halogenated aromatic hydrocarbon, an aliphatic hydrocarbon or a halogenated aromatic hydrocarbon.

26. A process according to claim 25 wherein the solvent is a dialkyl ether, an aromatic hydrocarbon, a chlorinated aromatic hydrocarbon, an aliphatic hydrocarbon, a chlorinated aliphatic hydrocarbon or a brominated aliphatic hydrocarbon.

27. A process according to claim 1 wherein the solvent is methylene chloride, chloroform or 1,2-dichloroethane.

28. A process according to claim 27 wherein the solvent is methylene chloride.

* * * * *